United States Patent [19]
Araki et al.

[11] Patent Number: 5,475,157
[45] Date of Patent: Dec. 12, 1995

[54] PROCESS FOR PRODUCING AROMATIC HYDROXYLIC COMPOUND

[75] Inventors: Shintaro Araki; Hiroshi Iwasaki; Hiroyasu Ohno; Isao Hashimoto, all of Yamaguchi; Teruaki Mukaiyama, Tokyo, all of Japan

[73] Assignee: Mitsui Petrochemical Industries, Ltd., Tokyo, Japan

[21] Appl. No.: 256,245

[22] PCT Filed: Nov. 1, 1993

[86] PCT No.: PCT/JP93/01586

§ 371 Date: Sep. 2, 1994

§ 102(e) Date: Sep. 2, 1994

[87] PCT Pub. No.: WO94/10115

PCT Pub. Date: May 11, 1994

[30] Foreign Application Priority Data

Nov. 5, 1992 [JP] Japan ................ 4-296146

[51] Int. Cl.⁶ .................... C07C 37/08; C07C 45/53
[52] U.S. Cl. .................... 568/798; 568/383; 568/385; 568/741; 568/768
[58] Field of Search .................... 568/798, 768, 568/741, 383, 385

[56] References Cited

U.S. PATENT DOCUMENTS

| | | | |
|---|---|---|---|
| 3,720,716 | 3/1973 | Shinohara et al. | 568/798 |
| 4,119,791 | 10/1978 | Hollingshead et al. | 568/768 |
| 4,267,379 | 5/1981 | Austin et al. | 568/385 |
| 4,267,380 | 5/1981 | Austin et al. | 568/385 |
| 4,358,618 | 11/1982 | Sifniades et al. | 568/385 |
| 4,434,305 | 2/1984 | Kurosaka et al. | 568/768 |
| 4,893,995 | 1/1990 | Hufstader | 417/370 |

FOREIGN PATENT DOCUMENTS

| | | |
|---|---|---|
| 0001043 | 3/1979 | European Pat. Off. |
| 0125065 | 11/1984 | European Pat. Off. |
| 1493977 | 4/1969 | Germany. |
| 421538 | 1/1942 | Japan. |
| 49-45854 | 12/1974 | Japan. |
| 50311 | 5/1975 | Japan. |
| 54-52041 | 4/1979 | Japan. |
| 57-95930 | 6/1982 | Japan. |
| 58-32831 | 2/1983 | Japan. |
| 60-84235 | 5/1985 | Japan. |
| 071662 | 9/1981 | United Kingdom. |

OTHER PUBLICATIONS

English Language Abstract of JP-A-50-50311 (May 6, 1975).
English Language Abstract of DE-A-1,493,977 Apr. 10, 1969.
English Language Abstract of JP-A-60-84235 May 13, 1985.

*Primary Examiner*—Werren B. Lone
*Attorney, Agent, or Firm*—Birch, Stewart, Kolasch & Birch

[57] ABSTRACT

There is disclosed a process for producing an aromatic hydroxylic compound by acid decomposition of a hydroperoxide having the general formula (I)

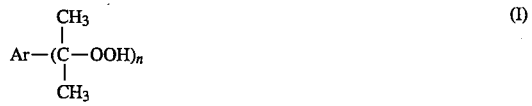

wherein Ar represents an aromatic hydrocarbon group having a valence of n; and n represents an integer of 1 or 2, in the presence of an acid catalyst, thereby to provide an aromatic hydroxylic compound having the general formula (II)

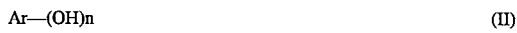

wherein Ar and n are the same as above defined, characterized in that tetrafluoroboric acid, hexafluorosilicic acid or hexafluorophosphoric acid is used as the acid catalyst. According to this process, the aromatic hydroxylic compound is obtained in a high yield while the by-production of hydroxyacetone is effectively suppressed. In paricular, a more effective suppression of by-production of hydroxyacetone and a higher yield of the target compound can be achieved by carrying out the acid decomposition reaction in two stages wherein the first stage of the reaction is carried out in the first reactor at a temperature of 50°–95° C., the resultant reaction mixture is sent to the second reactor, and the second stage of the reaction is then carried out in the second reactor at a temperature of 80°– 120° C.

20 Claims, No Drawings

PROCESS FOR PRODUCING AROMATIC HYDROXYLIC COMPOUND

This Application is a 371 of PCT 93/01583, Nov. 1, 1993.

1. Technical Field

This invention relates to a process for producing an aromatic hydroxylic compound useful for the production of synthetic resins, agricultural chemicals, dyestuffs or medicines.

2. Background Art

Among a number of processes for industrial production of aromatic hydroxylic compounds, there is known a process in which a hydroperoxide is decomposed in the presence of an acid catalyst. In this process, sulfuric acid has been mainly used as the acid catalyst, however, a variety of acid catalysts have been proposed other than sulfuric acid.

For instance, a process wherein trifluoromethanesulfonic acid is used as the acid catalyst is proposed in Japanese Patent Application Laid-open No. 50-50311. In addition, for instance, the use of an ion exchange resin containing sulfonic acid groups is proposed in U.S. Pat. No. 4,893,995, and the use of a variety of zeolites in European Patent No. 125,065. The use of Lewis acid such as stannic chloride, antimony chloride, sulfur tetrafluoride, silicon tetrafluoride or tungsten hexafluoride is proposed in U.S. Pat. No. 4,267,380, and a further Lewis acid such as boron trifluoride or boron trifluoride etherate in U.S. Pat. No. 4,267,379.

The decomposition of a hydroperoxide in the presence of an acid catalyst provides a ketone as well as an aromatic hydroxylic compound. In general, the decomposition of hydroperoxide having the general formula (I)

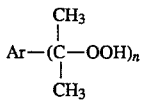
(I)

wherein Ar represents an aromatic hydrocarbon group having a valence of n; and n represents an integer of 1 or 2, produces acetone as the ketone. According to the conventional processes, the thus produced acetone readily reacts with the hydroperoxide as the starting material to by-produce hydroxyacetone. Thus, there arises a problem in the conventional industrial production of aromatic hydroxylic compound and acetone by the decomposition of hydroperoxide in the presence of an acid catalyst.

The first problem is that the yields of the aromatic hydroxylic compound and acetone are small. The second problem is that waste water contaminated with hydroxyacetone is generated as hydroxyacetone is water-soluble. The third problem is that the by-produced hydroxyacetone gets mixed with the resultant aromatic hydroxylic compound to lower its purity.

The invention has been accomplished to solve the above-mentioned problems involved in the conventional processes for production of an aromatic hydroxylic compound and acetone by the decomposition of hydroperoxide in the presence of an acid catalyst, and thus to provide a process which enables the production of an aromatic hydroxylic compound in a high yield with suppression of by-production of hydroxyacetone.

DISCLOSURE OF THE INVENTION

The invention provides a process for producing an aromatic hydroxylic compound by acid decomposition of a hydroperoxide having the general formula (I)

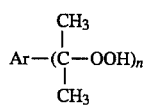
(I)

wherein Ar represents an aromatic hydrocarbon group having a valence of n; and n represents an integer of 1 or 2, in the presence of an acid catalyst, thereby to provide an aromatic hydroxylic compound having the general formula (II)

(II)

wherein Ar and n are the same as above defined, characterized in that tetrafluoroboric acid, hexafluorosilicic acid or hexafluorophosphoric acid is used as the acid catalyst.

In the above general formula, Ar represents an aromatic hydrocarbon group having a valence of n; and n represents an integer of 1 or 2.

Accordingly, when n is 1, Ar is, for example, phenyl; an alkyl substituted phenyl such as tolyl, isopropylphenyl, t-butylphenyl or diisopropylphenyl, a phenyl substituted phenyl such as phenylphenyl; an alkoxy or aryloxy substituted phenyl such as methoxyphenyl or phenoxyphenyl; naphthyl; an alkyl substituted naphthyl such as methylnaphthyl or isopropylnaphthyl; or a phenyl substituted naphthyl such as phenylnaphthyl. When n is 2, Ar is, for example, phenylene; an alkyl substituted phenylene such as methylphenylene or isopropylphenylene; naphthylene; an alkyl substituted naphthylene such as methylnaphthylene or isopropylnaphthylene; or a phenyl substituted naphthylene such as phenylnaphthylene.

The preferred hydroperoxide among the above represented by the general formula (I) in the process of the invention includes, for example, cumene hydroperoxide, cymene hydroperoxide, diisopropylbenzene monohydroperoxide, triisopropylbenzene monohydroperoxide, isopropylnaphthalene hydroperoxide, methylisopropylnaphthalene monohydroperoxide, diisopropylnaphthalene monohydroperoxide, diisopropylbenzene dihydroperoxide, triisopropylbenzene dihydroperoxide or diisopropylnaphthalene dihydroperoxide. These hydroperoxides may be produced by oxydation of the corresponding isopropyl substituted aromatic compounds with the air or molecular oxygen.

The aromatic hydroxylic compound having the general formula (II) which is produced according to the process of the invention includes, for example, phenol, cresol, isopropylphenol, diisopropylphenol, naphthol, methylnaphthol, isopropylnaphthol, resorcinol, hydroquinone, isopropyl resorcinol or dihydroxynaphthalene, corresponding to the hydroperoxide used.

The important feature of the process of the invention is that in the decomposition of the hydroperoxide in the presence of an acid catalyst, tetrafluoroboric acid (HBF$_4$), hexafluorosilicic acid (H$_2$SiF$_6$) or hexafluorophosphoric acid (HPF$_6$) is used as the acid catalyst.

In the process of the invention, such a protonic acid containing fluorine atoms therein as above mentioned is used as the acid catalyst. Since the hydroperoxide decomposes promptly in the presence of such a protonic acid, the protonic acid is used usually as a purified acid. However, as the case may be, a crude acid may be used. Taking tetrafluoroboric acid as an example, a crude form thereof may be a reaction product obtained by admixing hydrofluoric acid (HF) and boric acid (H$_3$BO$_3$) both in theoretical amounts in water at room temperatures.

Usually the acid catalyst is prepared as an aqueous solution or it is diluted with a solvent inactive to the reaction, and is then added to the reaction system.

The amount of the acid catalyst used is usually in the range of 20 ppm to 5% by weight, preferably of 100 ppm to 2% by weight, based on the reaction mixture. As well known, a hydroperoxide may be obtained in the form of solution which may contain a trace or small amount of by-products and the unreacted hydrocarbon by oxidizing the corresponding hydrocarbon as a starting material with molecular oxygen, for instance, with the air, in the presence of an aqueous alkaline solution under heating, and thereafter effecting oil-water separation, and then concentrating the separated oily product. Therefore, the reaction mixture means herein a mixture composed of solution of the hydroperoxide used and a catalyst (and a solvent, if used). The optimum amount of catalyst used depends upon the catalyst and reaction solvent used, reaction temperature, the amount of water in the reaction system and reaction time among others.

In the process of the invention, a reaction solvent may not be used. However, if necessary, a reaction solvent may be used which is stable under the reaction conditions under which the process of the invention is carried out. The solvent usable includes, for example, a ketone such as acetone; an aromatic hydrocarbon such as benzene, toluene or cumene; an aliphatic hydrocarbon such as hexane, heptane or octane; a cycloaliphatic hydrocarbon such as cyclohexane, methylcyclohexane or cyclooctane; a halogenated hydrocarbon such as dichloroethane or chlorobenzene; a phenolic compound such as phenol or cresol. The solvent may be used singly or as a mixture.

If a solvent is used, it is used in an amount preferably of 0.1–5 parts by weight per part by weight of the hydroperoxide used.

The reaction may be carried out batchwise or continuously. When the reaction is carried out continuously, the reactor used may be composed of a single vessel or a plurality of vessels, or a tubular reactor. If necessary, the reactor may be a combination of a vessel reactor and a tubular reactor.

When the reaction is carried out batchwise or continuously by use of a single vessel reactor, the reaction temperature is usually in the range of 20°–150° C., preferably in the range of 50°–140° C. The reaction time is usually in the range of 1 minute to 1 hour.

According to the invention, it is preferred that the first stage of the reaction is carried out in the first reactor, for example, in a continuous type vessel reactor, at a temperature of 50°–95° C., and then the second stage of the reaction is carried out in a second reactor, for example, in a tubular reactor, at a temperature of 80°–120° C., so that the by-production of hydroxyacetone is more effectively suppressed and a higher yield of the target aromatic hydroxylic compound is achieved.

In carrying out the reaction in two stages as set forth above, the first stage of the reaction is ceased when the concentration of the hydroperoxide remaining in the reaction mixture becomes not more than 1% by weight, preferably not more than 0.5% by weight, and then the second stage of the reaction is carried out until the concentration of the hydroperoxide remaining in the reaction mixture becomes not more than 0.1% by weight. In this manner, especially desirable results are obtained.

The reaction may be carried out under a reduced, normal or increased pressure, irrespectively of the manners as above mentioned in which the reaction is carried out.

After the completion of the reaction, the resultant reaction mixture is neutralized or washed with water to remove the acid catalyst therefrom, and is then concentrated, followed by distillation, crystallization or other suitable operations, to separate the aromatic hydroxylic compound.

INDUSTRIAL AVAILABILITY

According to the process of the invention for producing an aromatic hydroxylic compound and acetone by decomposing a hydroperoxide in the presence of an acid catalyst, the acid catalyst is selected from among tetrafluoroboric acid, hexafluorosilicic acid and hexafluorophosphoric acid, and hence the aromatic hydroxylic compound is obtained in a high yield while the by-production of hydroxyacetone is effectively suppressed.

A more effective suppression of by-production of hydroxyacetone and a higher yield of the target compound can be achieved by carrying out the acid decomposition reaction in two stages. Namely, the first stage of the reaction is carried out in the first reactor at a temperature of 50°–95° C., the resultant reaction mixture is sent to the second reactor, and then the second stage of the reaction is carried out in the second reactor at a temperature of 80°–120 C.

The invention will now be described with reference to examples, however, the invention is not limited thereto. Hereinafter the concentration of catalyst is indicated by a concentration in a reaction mixture, and the concentration of hydroxyacetone is indicated by a weight ratio to the aromatic hydroxylic compound obtained as the reaction product (target compound).

REFERENCE EXAMPLE 1

Cumene was air-oxidized at 100°–110° C. in the presence of an aqueous solution of sodium carbonate. After the reaction, oil-water separation was conducted, and the oily product was concentrated to provide a solution of cumene hydroperoxide (CHP) of which composition is indicated in Table 1.

TABLE 1

| Composition | Concentration (% by weight) |
| --- | --- |
| Cumene hydroperoxide (CHP) | 80.39 |
| Dicumyl peroxide (DCP) | 0.75 |
| Dimethylphnylcarbinol (DMPC) | 7.41 |
| Acetophenone | 0.94 |
| Cumene | 10.29 |
| Others | 0.22 |

EXAMPLE 1

Into a single vessel reactor of stainless having a 60 ml hold-up capacity for use in a continuous reaction and provided with a stirrer, a water cooling condenser, a warm water jacket, a temperature detector, an inlet tube for a feed material, an inlet tube for a catalyst and an outlet tube for extracting a reaction mixture, the solution of CHP prepared in the reference example 1 was added at a rate of 120 ml per hour and an acetone solution containing 1.01% by weight of tetrafluoroboric acid (421% aqueous solution) at a rate of 52 ml per hour. The concentration of tetrafluoroboric acid in the reaction mixture was 1200 ppm. The reaction was carried out in this manner with a hold-up time of 20 minutes while the reaction mixture was maintained at a temperature of 75° C.

The reaction mixture was extracted continuously from the reactor and neutralized with sodium carbonate powder, and then the amount of phenol and hydroxyacetone contained in the supernatant was analyzed by gas chromatography. The yield of phenol (based on the total moles of starting hydroperoxide, CHP, and dicumyl peroxide (DCP), the same hereinafter) was found to be .97 mol %, and the by-proction of hydroxyacetone (weight ratio to phenol, the same hereinafter) was found to be 390 ppm.

EXAMPLES 2, 3 AND COMPARATIVE EXAMPLES 1–5

The acid catalyst as indicated in Table 2 was used in place of tetrafluoroboric acid, and otherwise in the same manner as in Example 1, the reaction was carried out and the reaction mixture was analyzed. The results are indicated in Table 2.

TABLE 2

| | Catalyst | Concentration of Catalyst (ppm) | Yield of Phenol (%) | Concentration of Hydroxyacetone (ppm)*) |
|---|---|---|---|---|
| Example | | | | |
| 2 | $H_2SiF_6$ | 4000 | 97 | 460 |
| 3 | $HPF_6$ | 3000 | 97 | 720 |
| Comparative Example | | | | |
| 1 | $H_2SO_4$ | 2000 | 95 | 8700 |
| 2 | $BF_3 \cdot OEt_2$ | 1200 | 95 | 3300 |
| 3 | HF | 8000 | 67 | 2400 |
| 4 | $SiF_4$ | 4000 | 70 | 2000 |
| 5 | $CF_3SO_3H$ | 1000 | 97 | 1900 |

*)Weight ratio to phenol

EXAMPLE 4 AND COMPARATIVE EXAMPLES 6, 7

Cymene hydroperoxide was used in the form of solution in cymene as a starting material, and the acid catalyst as indicated in Table 3 was used, and otherwise in the same manner as in Example 1, the reaction was carried out and the reaction mixture was analyzed. The results are indicated in Table 3.

TABLE 3

| | Catalyst | Concentration of Catalyst (ppm) | Yield of Cresol (%) | Concentration of Hydroxyacetone (ppm)*) |
|---|---|---|---|---|
| Example 4 | $HBF_4$ | 1200 | 92 | 470 |
| Comparative Example | | | | |
| 6 | $H_2SO_4$ | 2000 | 90 | 9800 |
| 7 | $BF_3 \cdot OEt_2$ | 1200 | 91 | 3500 |

*)Weight ratio to cresol

EXAMPLE 5 AND COMPARATIVE EXAMPLES 8, 9 m-Diisopropylbenzene dihydroperoxide was used in the form of solution in m-diisopropylbenzene as a starting material and the acid catalyst as indicated in Table 4 was used, and otherwise in the same manner as in example 1, the reaction was carried out and the reaction mixture was analyzed. The results are indicated in Table 4.

TABLE 4

|  | Catalyst | Concentration of Catalyst (ppm) | Yield of Resorcinol (%) | Concentration of Hydroxyacetone (ppm)[*] |
|---|---|---|---|---|
| Example 4 | $HBF_4$ | 1200 | 80 | 550 |
| Comparative Example |  |  |  |  |
| 8 | $H_2SO_4$ | 2000 | 74 | 13200 |
| 9 | $BF_3 \cdot OEt_2$ | 1200 | 75 | 5100 |

[*] Weight ratio to resorcinol

EXAMPLE 6

Into a single vessel reactor (the first reactor) of stainless having a 100 ml hold-up capacity for use in a continuous reaction and provided with a stirrer, a water cooling condenser, a warm water jacket, a temperature detector, an inlet tube for a feed material, an inlet tube for a catalyst and an outlet tube for extracting a reaction mixture, the solution of CHP prepared in the reference example 1 was added at a rate of 260 g per hour and an acetone solution containing 0.15% by weight of tetrafluoroboric acid and 1.6% by weight of water at a rate of 40.9 g per hour. The concentration of tetrafluoroboric acid in the reaction mixture was 200 ppm. The reaction was carried out in this manner with a hold-up time of 20 minutes while the reaction mixture was maintained at a temperature of 84° C.

The reaction mixture was extracted continuously from the first reactor and neutralized with sodium carbonate powder, and then the composition of the supernatant was analyzed by gas chromatography. The results are indicated in Table 5.

TABLE 5

| Composition | Concentration (% by weight) |
|---|---|
| Phenol | 41.47 |
| Acetone | 38.00 |
| Cumene | 8.92 |
| DCP | 4.47 |
| α-Methylstyrene | 2.40 |
| Acetophenone | 0.94 |
| DMPC | 0.74 |
| CHP | 0.31 |
| Others | 2.75 |

The reaction mixture extracted continuously from the first reactor was sent with a pressure pump into a coiled stainless tube having an inside diameter of 4 mm (the second reactor) provided with a temperature detector and a pressure gage and immersed in a heated oil bath, with an inside volume of 20 ml in the oil bath. The reaction was carried out in this manner with a hold-up time of 4 minutes while the reaction mixture was maintained at a temperature of 116° C.

The reaction mixture was extracted continuously from the second reactor through a water-cooling jacket and a pressure release valve, and was neutralized with sodium carbonate powder. The composition of the supernatant was then analyzed by gas chromatography. The results are indicated in Table 6.

TABLE 6

| Composition | Concentration (% by weight) |
|---|---|
| Phenol | 42.96 |
| Acetone | 39.33 |
| Cumene | 8.94 |
| DCP | 0.73 |
| α-Methylstyrene | 3.45 |
| Acetophenone | 1.08 |
| DMPC | 0.33 |
| CHP | 0.01 |
| Others | 3.17 |

In a manner as above set forth the acid decomposition was conducted in two stages by use of the first and second reactor. As results, the yield of phenol was found to be 99%. From the analysis of the other components in Table 6, the by-production of hydroxyacetone was found to be 240 ppm.

COMPARATIVE EXAMPLE 10

Sulfuric acid was used in place of tetrafluoroboric acid, and otherwise in the same manner as in Example 6, the reaction was carried out and the reaction mixture was analyzed. The yield of phenol was found to be 97%, and the by-production of hydroxyacetone was found to be 2000 ppm.

We claim:

1. A process for producing an aromatic hydroxylic compound comprising the step of decomposing a hydroperoxide having the formula (I)

wherein Ar represents an aromatic hydrocarbon group having a valence of n; and n represents an integer of 1 or 2,
in the presence of an acid catalyst to thereby obtain an aromatic hydroxylic compound having the formula (II)

wherein Ar and n are the same as above defined,
wherein the acid catalyst is selected from the group consisting of tetrafluoroboric acid, hexafluorosilicic acid and hexafluorophosphoric acid.

2. The process for producing an aromatic hydroxylic compound according to claim 1, wherein the acid catalyst is used in an amount of 20 ppm to 5% by weight based on the reaction mixture.

3. The process for producing an aromatic hydroxylic compound according to claim 1, wherein, in the formula (I), when n is 1, Ar is phenyl or a substituted phenyl, and when n is 2, Ar is phenylene, a substituted phenylene, naphthylene or a substituted naphthylene.

4. The process for producing an aromatic hydroxylic compound according to claim 2, wherein, in the formula (I), when n is 1, Ar is phenyl or a substituted phenyl, and when n is 2, Ar is phenylene, a substituted phenylene, naphthylene or a substituted naphthylene.

5. The process for producing an aromatic hydroxylic compound according to claim 1, wherein the hydroperoxide is selected from the group consisting of cumene hydroperoxide, cymene hydroperoxide, diisopropylbenzene monohydroperoxide, triisopropylbenzene monohydroperoxide, isopropylnaphthalene hydroperoxide, methylisopropylnaphthalene monohydroperoxide, diisopropylnaphthalene monohydroperoxide, diisopropylbenzene dihydroperoxide, triisopropylbenzene dihydroperoxide and diisopropylnaphthalene dihydroperoxide.

6. The process for producing an aromatic hydroxylic compound according to claim 2, wherein the hydroperoxide is selected from the group consisting of cumene hydroperoxide, cymene hydroperoxide, diisopropylbenzene monohydroperoxide, triisopropylbenzene monohydroperoxide, isopropylnaphthalene hydroperoxide, methylisopropylnaphthalene monohydroperoxide, diisopropylnaphthalene monohydroperoxide, diisopropylbenzene dihydroperoxide, triisopropylbenzene dihydroperoxide and diisopropylnaphthalene dihydroperoxide.

7. The process for producing an aromatic hydroxylic compound according to claim 1, wherein the hydroperoxide is cumene hydroperoxide.

8. The process for producing an aromatic hydroxylic compound according to claim 1, wherein the hydroperoxide is cymene hydroperoxide.

9. The process for producing an aromatic hydroxylic compound according to claim 1, wherein the hydroperoxide is diisopropylbenzene dihydroperoxide.

10. A process for producing an aromatic hydroxylic compound comprising a two-stage step of decomposing a hydroperoxide having the formula (I)

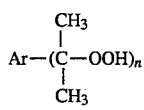

wherein Ar represents an aromatic hydrocarbon group having a valance of n; and n represents an integer of 1 or 2,
in the presence of an acid catalyst to thereby obtain an aromatic hydroxylic compound having the formula (II)

Ar—(OH)$_n$     (II)

wherein Ar and n are the same as above defined, wherein the acid catalyst is selected from the group consisting of tetrafluoroboric acid, hexafluorosilicic acid and hexafluorophosphoric acid; and the first stage of the reaction is carried out in a first reactor at a temperature of 50°–95° C., the second stage of the reaction is carried out in a second reactor at a temperature of 80°–120° C., and the reaction mixture from the first reactor is sent to the second reactor.

11. The process for producing an aromatic hydroxylic compound according to claim 10, wherein the first stage of the reaction is terminated when the concentration of the hydroperoxide in the reaction mixture becomes not more than 1% by weight, and the second stage of the reaction is carried out until the concentration of the hydroperoxide in the reaction mixture becomes not more than 0.1% by weight.

12. The process for producing an aromatic hydroxylic compound according to claim 10, wherein the acid catalyst is used in an amount of 20 ppm to 5% by weight based on the reaction mixture.

13. The process for producing an aromatic hydroxylic compound according to claim 11, wherein the acid catalyst is used in an amount of 20 ppm to 5% by weight based on the reaction mixture.

14. The process for producing an aromatic hydroxylic compound according to claim 10, wherein, when n is 1, Ar is phenyl or a substituted phenyl, and when n is 2, Ar is phenylene, a substituted phenylene, naphthylene or a substituted naphthylene.

15. The process for producing an aromatic hydroxylic compound according to claim 11, wherein, when n is 1, Ar is phenyl or a substituted phenyl, and when n is 2, Ar is phenylene, a substituted phenylene, naphthylene or a substituted naphthylene.

16. The process for producing an aromatic hydroxylic compound according to claim 10, wherein the hydroperoxide is selected from the group consisting of cumene hydroperoxide, cymene hydroperoxide, diisopropylbenzene monohydroperoxide, triisopropylbenzene monohydroperoxide, isopropylnaphthalene hydroperoxide, methylisopropylnaphthalene monohydroperoxide, diisopropylnaphthalene monohydroperoxide, diisopropylbenzene dihydroperoxide, triisopropylbenzene dihydroperoxide and diisopropylnaphthalene dihydroperoxide.

17. The process for producing an aromatic hydroxylic compound according to claim 11, wherein the hydroperoxide is selected from the group consisting of cumene hydroperoxide, cymene hydroperoxide, diisopropylbenzene monohydroperoxide, triisopropylbenzene monohydroperoxide, isopropylnaphthalene hydroperoxide, methylisopropylnaphthalene monohydroperoxide, diisopropylnaphthalene monohydroperoxide, diisopropylbenzene dihydroperoxide, triisopropylbenzene dihydroperoxide and diisopropylnaphthalene dihydroperoxide.

18. The process for producing an aromatic hydroxylic compound according to claim 10, wherein the hydroperoxide is cumene hydroperoxide.

19. The process for producing an aromatic hydroxylic compound according to claim 10, wherein the hydroperoxide is cymene hydroperoxide.

20. The process for producing an aromatic hydroxylic compound according to claim 10, wherein the hydroperoxide is diisopropylbenzene dihydroperoxide.

* * * * *